United States Patent [19]

Leighton et al.

[11] Patent Number: 5,301,671
[45] Date of Patent: Apr. 12, 1994

[54] TWO- AND THREE-DIMENSIONAL AUTORADIOGRAPHIC IMAGING UTILIZING CHARGE COUPLED DEVICES

[75] Inventors: Stephen B. Leighton, Maplewood, N.J.; James L. Olds, Bethesda, Md.

[73] Assignee: The United States of America as represented by the Department of Health and Human Services, Washington, D.C.

[21] Appl. No.: 761,157

[22] Filed: Sep. 17, 1991

[51] Int. Cl.$^5$ .............................................. A61B 5/00
[52] U.S. Cl. ............................... 128/654; 250/363.02; 250/370.01
[58] Field of Search ..................... 128/653.1, 654, 659; 250/336.1, 363.1, 363.01, 363.02, 363.04, 370.01

[56] References Cited

U.S. PATENT DOCUMENTS

| | | |
|---|---|---|
| 3,678,148 | 7/1972 | Caiola . |
| 3,876,882 | 4/1975 | Todd . |
| 4,224,303 | 9/1980 | Shaw . |
| 4,377,958 | 3/1983 | Leighton . |
| 4,476,231 | 10/1984 | Deindoerfer et al. . |
| 4,517,976 | 5/1985 | Murakoshi et al. ..................... 128/4 |
| 4,595,014 | 6/1986 | Barrett et al. . |
| 4,611,247 | 9/1986 | Ishida et al. . |
| 4,622,954 | 11/1986 | Arakawa et al. ........................ 128/6 |
| 4,623,288 | 11/1986 | Brunelli et al. ...................... 128/659 |
| 4,833,327 | 5/1989 | Hart . |
| 4,889,991 | 12/1989 | Ramsey et al. . |
| 4,893,013 | 1/1990 | Denen et al. . |
| 4,976,266 | 12/1990 | Huffman et al. . |
| 4,995,396 | 2/1991 | Inaba et al. . |
| 5,005,195 | 4/1991 | Lanza et al. . |
| 5,014,708 | 5/1991 | Hayashi et al. ...................... 128/659 |
| 5,028,793 | 7/1991 | Lindmayer et al. . |
| 5,070,878 | 12/1991 | Denen . |
| 5,103,823 | 4/1992 | Acharya et al. . |
| 5,119,818 | 6/1992 | Carroll et al. . |

OTHER PUBLICATIONS

Leighton, "Sem Images of Block Faces, Cut By A Miniature Microtom Within The Sem—A Technical Note", *Scanning Electron Microscopy II*, (1981), pp. 73-76.
Leighton, "A Miniature Microtome For Use Inside A Scanning Electron Microscope", *Advances in BioEngineering*, (1981), pp. 45 and 46.
Leighton, "Oxygen Plasma Etching of Entire Block Faces Improves the Resolution and Usefulness of Serial Scanning Electron Microscope Images", *Scanning Electron Microscopy*, (1983), pp. 1877-1885.
Leighton et al., "A Systematic Method For Scanning Electron Microscope Examination Of Embedded Issue", *Biological Bulletin*, (1987), vol. 173, p. 444.
Texas Instruments, *Solid State Image Sensor*, (Oct. 1987).
Charon et al., "A High Resolution $\beta$Detector", *Nuclear Instruments and Methods In Physics Research*, A273 (1988), pp. 748-753.

*Primary Examiner*—Kyle L. Howell
*Assistant Examiner*—Krista Pfaffle
*Attorney, Agent, or Firm*—Lowe, Price, LeBlanc & Becker

[57] ABSTRACT

A two- and three-dimensional autoradiographical imaging system is provided which includes a charge coupled device for detecting the emission of radioactively labeled substances from materials such as tissue samples, brains of humans or animals, or substances used in electrophoresis applications. In a first aspect, a radioactively labeled substance is included in a tissue sample. The tissue sample is sequentially imaged by a charge coupled device and a sectioning tool such as a microtome to produce a plurality of two-dimensional images. A three-dimensional image of the tissue sample is generated by further processing of the plurality of two-dimensional images derived from the charge coupled device. In a further aspect of the invention, a charge coupled device is utilized to provide realtime imaging of metabolic or physiological parameters involved in brain activity. A charge coupled device is positioned adjacent a portion of brain tissue desired to be examined, the brain tissue having a radioactively labeled substance therein for detection by the charge coupled device. A two-dimensional realtime image is produced using the charge coupled device for use in clinical or behavioral studies.

26 Claims, 6 Drawing Sheets

TWO- AND THREE-DIMENSIONAL AUTORADIOGRAPHIC IMAGING UTILIZING CHARGE COUPLED DEVICES

FIELD OF THE INVENTION

The present invention is directed to the utilization of charge coupled devices for improved two- and three-dimensional autoradiographic imaging. In a first aspect, a CCD is used in combination with a microtome to produce a three-dimensional map of a body tissue sample. In a second aspect, a CCD is utilized to provide two-dimensional realtime imagery of metabolic or biochemical parameters associated with the brains of humans or animals. In a third aspect, a CCD is used in connection with an electrophoresis process and radioactively tagged analytes to facilitate clinical determinations and investigations.

BACKGROUND ART

In the prior art, numerous methods and apparatus have been proposed to produce a three-dimensional map or image of a distribution of radioactively tagged chemical substances. U.S. Pat. No. 4,833,327 to Hart discloses a high-resolution radioisotopic imaging system. The system accurately reconstructs using a high spatial resolution three-dimensional distributor of radioactivity of the kind encountered in lesion detection in nuclear medicine. A key feature of the invention is a plurality of electronic collimator detector elements arranged about a radioisotopic source field of radioisotopic atoms, each operating for simultaneously emitting a plurality of gamma-rays.

U.S. Pat. No. 5,005,195 to Lanza et al. discloses a method of determining bone mineral content, which is an indication of osteoporosis, using radiography. FIG. 3 thereof shows a detector module 14 capable of determining the optical intensity of radiation emitted by a radiation source and transmitted through a patient's limb. The patient's limbs are positioned between blocks, one block simulating bone and another block simulating tissue. A readout system for the detector is provided which includes a gating mechanism that receives signals simultaneously generated at a plurality of locations within the detector in response to a radiation event and an estimating mechanism for identifying the focus of the radiation event from the signals.

U.S. Pat. No. 4,611,247 to Ishida et al. discloses a radiation image reproducing apparatus that permits optical processed imagery to be reproduced. The image of an object is stored as a latent image from a recording medium such as a phosphorous sheet stimulated by radiation transmitted through the object. A reader exposes the recording medium to stimulating rays and photoelectrically reads the resulting light and enters the object's image onto an apparatus in the form of video signals. A processing unit is employed for processing various factors associated with images, such as gradation and spatial frequency.

U.S. Pat. No. 4,476,231 to Deindoerfer et al. discloses a method of analyzing a distribution of a reagent between particles and liquids in a suspension. The reagent may be labeled with a radioactive isotope which emits gamma-radiation. The apparatus includes a body containing a flow chamber having an examination area. A microscope is focused on the examination area, which is illuminated by a strobe light. The output of the microscope is focused on a CCD camera. The output from the CCD camera is converted to a series of still frame images. Electronic processors are used for evaluating these images and include a television monitor and frame grabber. The frame grabber stores the images of the subject used by the CCD.

U.S. Pat. Nos. 4,224,303 to Shaw, 3,876,882 to Todd, and 3,678,148 to Caiola disclose utilizing a radioactive material to track and/or analyze an analyte for medical or clinical investigation. In these patents, the radioactive particles are detected and displayed. In U.S. Pat. No. 4,224,303 to Shaw, the cumulative data from detection of the radioactive particles is produced into a three-dimensional representation of a lumen of a coronary arterial system.

The prior art also recognizes producing a three-dimensional image utilizing the combination of a microtome and scanning electron microscopy.

U.S. Pat. No. 4,377,958 to Leighton discloses a miniature microtome assembly in which the circuits of a sample section are optically observed by an operator's eye or by means of a camera. The disclosure of this patent is herein incorporated by reference for purposes of disclosing that which is well known in the art with respect to microtome apparatus.

The publication entitled "SEM Images of Block Faces, Cut by a Miniature Microtome Within the SEM—a Technical Note", Scanning Electron Microscopy II (1981), pages 73–76, by Leighton, discloses the use of a scanning electron microscope (SEM) to image successive surfaces of a sample section with a miniature microtome. This reference discusses the implications for a three-dimensional reconstruction of a sample as imaged by the scanning electron-microscope.

However, a need has developed in biological and other research to provide three-dimensional maps of the distribution of radioactively tagged chemical substances in order to determine the distribution of chemicals and other substances in a tissue or other matrix being studied. In response to this need, an apparatus and method have been developed for automatically and efficiently producing three-dimensional maps derived from the detection of radioactively tagged substances. The improved autoradiographic imaging method and apparatus include utilizing a charge coupled device in combination with a microtome to obtain a two-dimensional image of a body tissue sample. The microtome subsequently provides a series of tissue surfaces to be read by the charge coupled device to produce a series of two-dimensional views of the tissue sample. Image processing means produces a three-dimensional view from the series of two-dimensional images produced from the tissue samples.

As described above in U.S. Pat. No. 4,476,231 to Deindoerfer et al. and in U.S. Pat. No. 4,995,396 to Inaba et al., the prior art has proposed utilizing a CCD for detection of radioactivity. In the Inaba et al. patent, an imaging solid state imaging device, as, for example, a CCD, is used simultaneously as a radioactive ray detecting means. That is to say, when radioactive rays as gamma-rays enter the CCD, these radioactive rays will contact a PN-junction in the light-receiving part of the CCD and will issue a signal, the signal being translated to appear on a picture surface of a monitor as a bright point. Inaba et al. does not image but rather merely detects radiation. The radiation detection gives no information on the location of the radiation source other than the general direction in which the CCD as a whole is known to be pointing.

Although the prior art has proposed utilizing charge coupled devices or CCDs in conjunction with the detection of radioactive rays such as gamma-rays or the like, a need has developed for improved detection of biochemical or physiological parameters in the brains of humans and animals using real-time imagery. In response to this need, an improved in-vivo autoradiography method and apparatus has been developed which permits monitoring of these types of parameters over time while producing a two-dimensional image. A radioactively labeled substance is administered to a brain and changing patterns are continuously recorded using a charge coupled device.

In the field of electrophoresis, the prior art has also proposed imaging screens for detecting and storing information corresponding to a pattern of emission from an electrophoresis gel containing radioactively labeled substances. U.S. Pat. No. 5,028,793 to Lindmayer et al. discloses an imaging screen for electrophoresis applications and, more particularly, to an imaging screen for detecting and recording the impingement of beta-particles or visible light emitted from electrophoresis gels. In the patent to Lindmayer et al., an imaging screen is placed on an electrophoresis gel containing radioactively labeled protein fragments. The beta particles of the radioactive substances or visible light impinge upon the surface of the imaging screen. The light emitted from the imaging screen by release of trapped electrons is detected by a visual light detector such as a photomultiplier tube with mechanical scanning in two directions. A CID camera alternative uses a CID camera to sense light, not radiation, requires lenses and an infrared light source. The method and apparatus of Lindmayer et al. requires an imaging screen which includes a coating of an electron trapping material for releasably storing information corresponding to the flux in pattern of the emission from the radioactively labeled substance in the electrophoresis gel.

A need has developed to provide more accurate and automatic means to monitor the radioactive emissions of substances used in electrophoresis applications. In response to this need, an electrophoresis apparatus and method have been developed which utilizes a two-dimensional charge coupled device for use with an electrophoresis gel including radioactively tagged substances such as low-energy beta emitters. By this combination, very small sample volumes are attainable, and automatic end-point detection may be achieved, thereby optimizing runs.

None of the prior art cited above teaches or fairly suggests the concept of producing a three-dimensional image of a tissue sample utilizing the combination of a charge coupled device and a tissue sectionizing apparatus. In addition, the prior art does not teach or fairly suggest the utilization of a charge coupled device for use in real-time imaging of metabolic or physiological parameters in the brains of humans and animals or radioactive emissions in electrophoresis applications.

SUMMARY OF THE INVENTION

It is a first object of the present invention to provide an improved method and apparatus for two- and three-dimensional autoradiographical imaging using a charge coupled device and radioactively labeled substances.

It is a further object of the present invention to provide a three-dimensional autoradiographical method and apparatus which includes producing a series of two-dimensional images of a tissue sample using a CCD and processing a plurality of the two-dimensional images to produce a three-dimensional image of the tissue sample.

It is a still further object of the present invention to provide an autoradiographic imaging method and apparatus which includes manipulating and control means to provide automatic sequencing and producing of a three-dimensional image by manipulating the charge coupled device, microtome and tissue sample, or a combination thereof.

It is a further object of the present invention to provide an autoradiographic imaging method and apparatus which provides a real-time two-dimensional image of physiological activity in a brain by monitoring a radioactively labeled substance therein using a charge coupled device.

It is a still further object of the present invention to provide a two-dimensional autoradiographic imaging system and apparatus applicable in electrophoresis gel investigations using radioactively labeled substances by monitoring radioactive emissions using a charge coupled device.

In satisfaction of the foregoing objects and advantages, there is provided an apparatus for producing a three-dimensional autoradiographic image of a tissue sample containing a radioactively tagged substance comprising a charge coupled device for producing a two-dimensional image of a portion of a tissue sample, a microtome for sectioning the tissue sample to provide a series of further exposed surfaces to be read by the charge coupled device, imaging means for producing an image from the information detected by the charge coupled device including a three-dimensional image from a plurality of sensed two-dimensional images and means to manipulate the sectioned portions of the tissue sample. Also provided are control means for integrating the charge coupled device, manipulation means and imaging means to produce a three-dimensional image of the tissue sample in automated fashion.

Also disclosed is a method for producing a three-dimensional autoradiographic image of a tissue sample containing a radioactively labeled substance which includes the steps of detecting a radioactively tagged substance using a charge coupled device in the tissue sample to produce a two-dimensional image. A plurality of two-dimensional images are obtained by manipulation of the tissue sample and sections thereof using a microtome knife. A plurality of two-dimensional images are processed to produce a three-dimensional image of the tissue sample.

In a further embodiment, a charge coupled device is utilized to monitor and provide real-time imagery of metabolic or physiological parameters in the brain of a human or an animal. In this aspect, a biocompatibly encapsulated charge coupled device is provided adjacent or within a brain to monitor a radioactively tagged substance administered to the brain either topically or systemically. A two-dimensional image of high resolution is produced which continually records changing parameter patterns within the brain. In a further embodiment, the biocompatibly encapsulated charge coupled device may be implanted within the brain and may also include a transmitter and receiver combination to provide telemetering of information through the skin and the skull of the human or animal for clinical or behavioral studies.

In a still further aspect of the present invention, a charge coupled device is utilized in an electrophoresis method and apparatus to produce a two-dimensional image of radioactively labeled substances such as low-energy Beta-emitters used in the electrophoresis. Use of a two-dimensional imaging CCD device facilitates the use of small sample volumes, automatic end point detection and eliminates post-run development requiring such techniques as staining.

BRIEF DESCRIPTION OF DRAWINGS

Reference is now made to the drawings accomplishing the application, wherein.

DESCRIPTION OF THE PREFERRED EMBODIMENTS

The present invention is concerned with two- and three-dimensional autoradiographical imaging of radioactively tagged substances in body tissue or electrophoresis application. In one aspect, a three-dimensional autoradiographic imaging method and apparatus is proposed which offers advantages over prior art devices including automated imaging as well as improved sequencing and processing techniques with body tissue samples.

In biological and other research, it is desirable to obtain three-dimensional maps of the distribution of substances, particularly radioactively labeled chemical species, in order to determine the distribution of chemicals and other substances in the tissue or other matrix being studied. In prior art devices, individual sections of a radioactively labeled tissue that is the subject of clinical investigation are cut and laid on photographic film for some exposure of time. The film is then developed and the sequence of images is compiled into a three-dimensional image or computer data-set. This method is slow, involves the recurring cost of the photographic film, and the difficulties in handling and aligning individual sections. In contrast, the proposed three-dimensional autoradiographical imaging system and method includes cutting and manipulating a section of a tissue sample and automatically aligning or placing a two-dimensional charge coupled device integrated circuit against an exposed surface of the tissue sample. An image of the radioactive source in the tissue sample is created in the array of elements of the CCD. This image is electronically transferred to a computer or storage device for further processing. In this three-dimensional imaging method and apparatus, imaging of each surface can range between only seconds to longer periods of time, depending on the amount of radioisotope in the tissue, individual sections do not have to be handled and alignment is intrinsic, since the tissue sample block may remain stationary during the overall processing and sectioning of the tissue sample to provide further exposed surfaces for clinical determinations.

Figure 1:
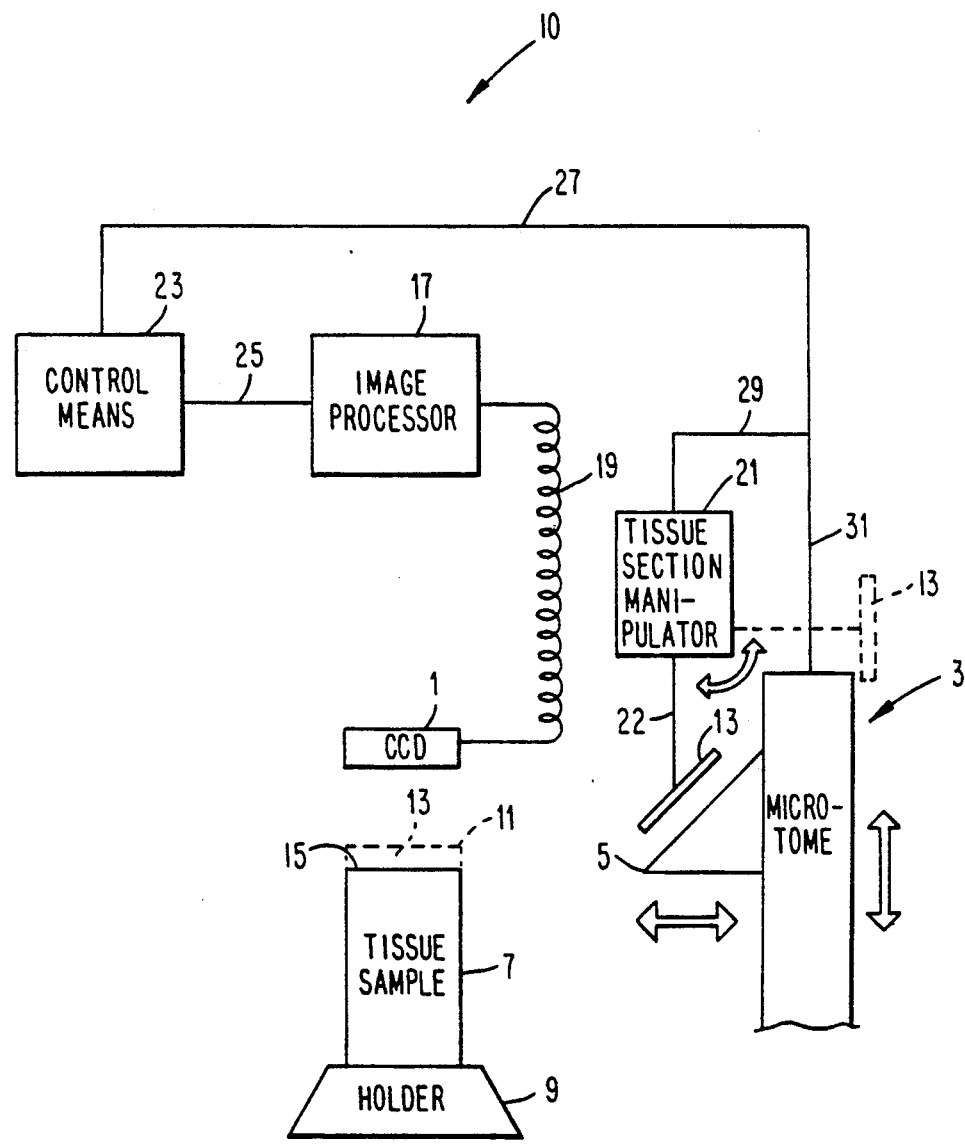
FIG. 1 shows a schematic representation of a first embodiment of a three-dimensional autoradiographic imaging apparatus.

With reference to FIG. 1, a schematic representation of a first embodiment of the three-dimensional autoradiographical imaging system is generally designated by the reference numeral 10 and is seen to include a charge coupled device 1 and a microtome assembly 3. The microtome assembly 3 includes a knife edge 5 thereon which is designed to section portions of a tissue sample 7. The tissue sample 7 is mounted on a sample block 9 and includes a top surface 11 thereon. The microtome assembly 3 is designed to remove a section 13 of the tissue sample 7 to expose a further surface 15 to the charge coupled device 1.

The charge coupled device is electrically and flexibly connected by the connector 19 to an image processor 17. It should be understood that the image processor 17 is of a type that is well known in the art as having the capability of processing information transmitted from a charge coupled device and processing the information into a two-dimensional image. In addition, the image processor includes the capability of storing a plurality of two-dimensional images detected by the charge coupled device and processing the plurality of dimensional images into a three-dimensional image of the tissue sample 7. The image processor may take the form of a computer or computer device which is capable of performing the functions as described above. For example, the CCD may be coupled to a frame grabber, a stand-alone computer or computer chip or array processor. Since these types of devices are well recognized in the art of producing two-dimensional images from information detected by a charge coupled device, a further description of the details is not included herewith.

The three-dimensional autoradiographic imaging system also includes a tissue section manipulator 21. As can be seen from FIG. 1, once the tissue section 13 is removed from the tissue sample 7 by the microtome 3, manipulation of the tissue section is required. The tissue section manipulator 21 is schematically shown with a manipulating arm 22 which, in one mode, removes the tissue section 13 from the travel of the microtome 3. As will be more completely described hereinafter, the tissue section 13 may be discarded or preserved for further clinical analysis or investigation.

The three-dimensional autoradiographical imaging system also includes a control means 23 which facilitates automatic imaging of respective tissue sections of the tissue sample 7. The control means 23 is connected to the image processor 17 by the electrical connection 25. In addition, the control means 23 is connected via the electrical connectors 27, 29 and 31 to the tissue section manipulator 21 and microtome 3, respectively. It should be understood that the control means 23 is considered to be a conventional type that is capable of controlling a plurality of apparatus elements and functions to operate in a particular and predetermined fashion. As will be described hereinafter, the control means is designed to control the operation of the image processor 17 in combination with the charge coupled device, tissue section manipulating means 21, microtome 3 and tissue sample 7 and sample holder 9 to provide an automatic sequencing and processing to produce the desired three-dimensional image.

The image processor 17, although not shown, may also include display means to visually display information detected by the charge coupled device as well as a data recorder means to accumulate and record data from the charge coupled device for further investigation.

An exemplary use of the first embodiment depicted in FIG. 1 will now be described. A tissue sample 7 containing an appropriate radioactively labeled substance therein may be mounted on the tissue sample block 9. Prior to sectioning of the tissue sample 7, the charge coupled device 1 reads the top surface 11 of the tissue sample 7 and transmits the information detected therefrom to the image processor 17. The image processor 17 produces a two-dimensional image of the radioactively labeled substance contained in the top surface 11 of the tissue sample 7. After this initial sequence, the microtome 3 is directed to remove a section 13 of a given thickness from the tissue sample 7. After the section 13 is removed, the tissue section manipulator 21 may either discard the section 13 or preserve it for further use. A further exposed surface 15 is then read by the charge coupled device 1 which transmits the information therefrom to the image processor 17. In this manner, a second and sequential two-dimensional image is obtained from the tissue sample 7. This series of sectioning and detecting of the radioactively labeled substance in the further exposed surface of the tissue sample 7 of the charge coupled device 1 is continued until the entire tissue sample 7 is analyzed by the CCD. After the image processor has received a plurality of two-dimensional images from the tissue sample 7, the image processor 17 processes the two-dimensional images into a three-dimensional image of the tissue sample 7. Given this three-dimensional image of the radioactively labeled substance in the tissue sample 7, clinical investigation may be performed for medical or research reasons. It should be noted that the CCD array is erased after each positioning against a newly cut surface of the tissue sample and transfer of the image information to the image processor. In addition, determination of the exposure time for the CCD can be determined empirically or extrapolated by appropriate calculations based upon initial tests and observations. Control of the exposure time is made through the control means 23 by the image processor 17 and the CCD 1.

Figure 2:
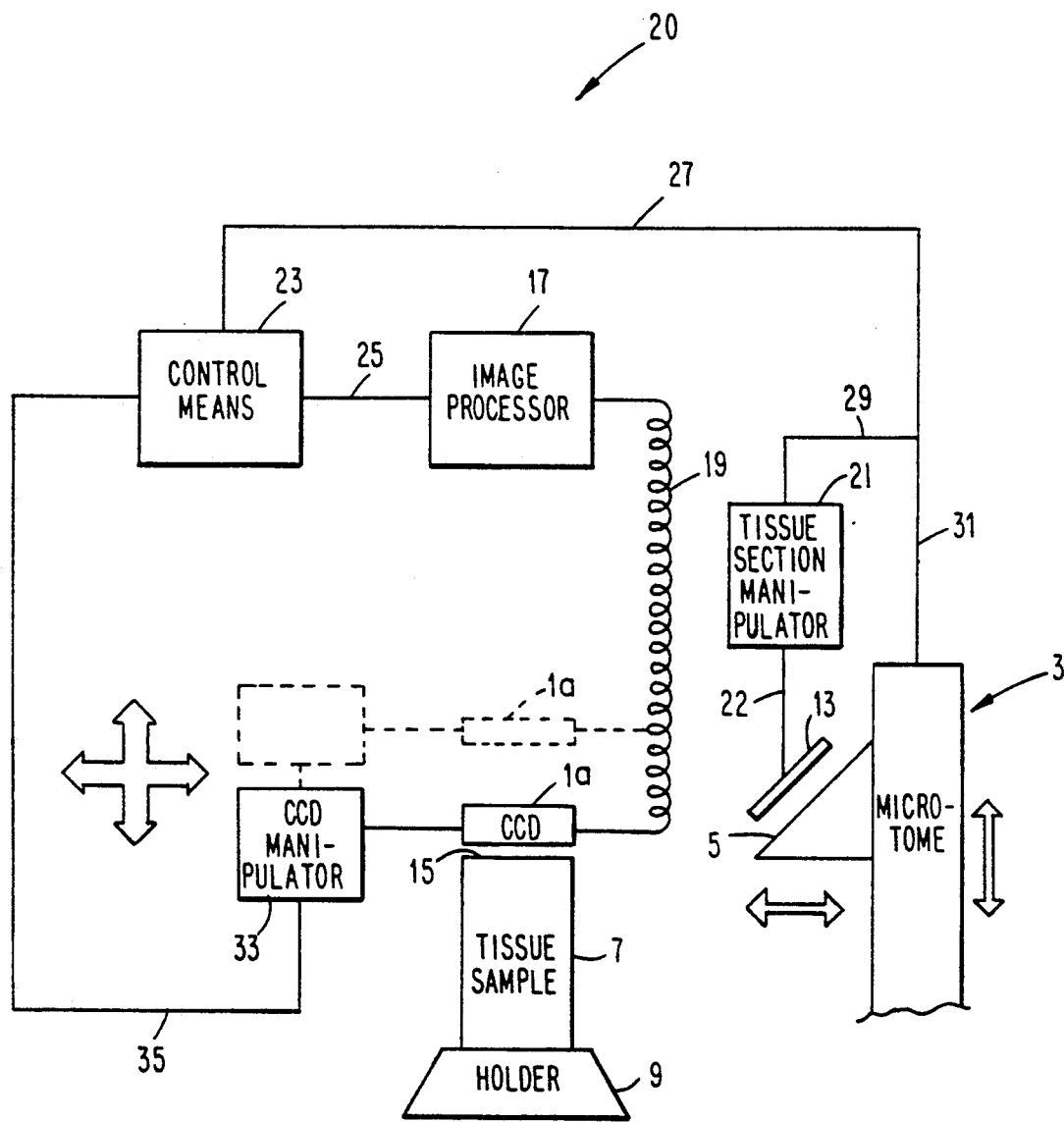
FIG. 2 shows a second embodiment of a three-dimensional autoradiographic imaging apparatus.

With reference to FIG. 2, a second embodiment of the three-dimensional autoradiographical imaging system is generally designated by the reference numeral 20 and is seen to include all of the components as illustrated in FIG. 1 with an additional CCD manipulating means 33. The CCD manipulating means 33 is designed to position the CCD 1a against the surface of the tissue sample 7 to be read for purposes of producing a two-dimensional image thereof. As depicted by the arrows in FIG. 2, the CCD manipulating means 33 may position the CCD 1a vertically or horizontally with respect to the tissue sample 7. The control means 23 is designed to control the movement of the manipulating means 33 via the connector 35.

In this embodiment, initially, the CCD is in the position depicted in cross-hatch. After a tissue sample 13 is cut and removed by the microtome 3 and tissue section manipulating means 21, the charge coupled device 1a is lowered by the charge coupled device manipulating means 33 in a position adjacent the top surface 15 of the tissue sample 7. The CCD 1a reads the radioactively tagged substances adjacent the surface 15 and transmits the information to the image processor 17. The same sequence of events and control thereof continues as described for the embodiment depicted in FIG. 1 to produce a three-dimensional image of the tissue sample 7.

Figure 3:
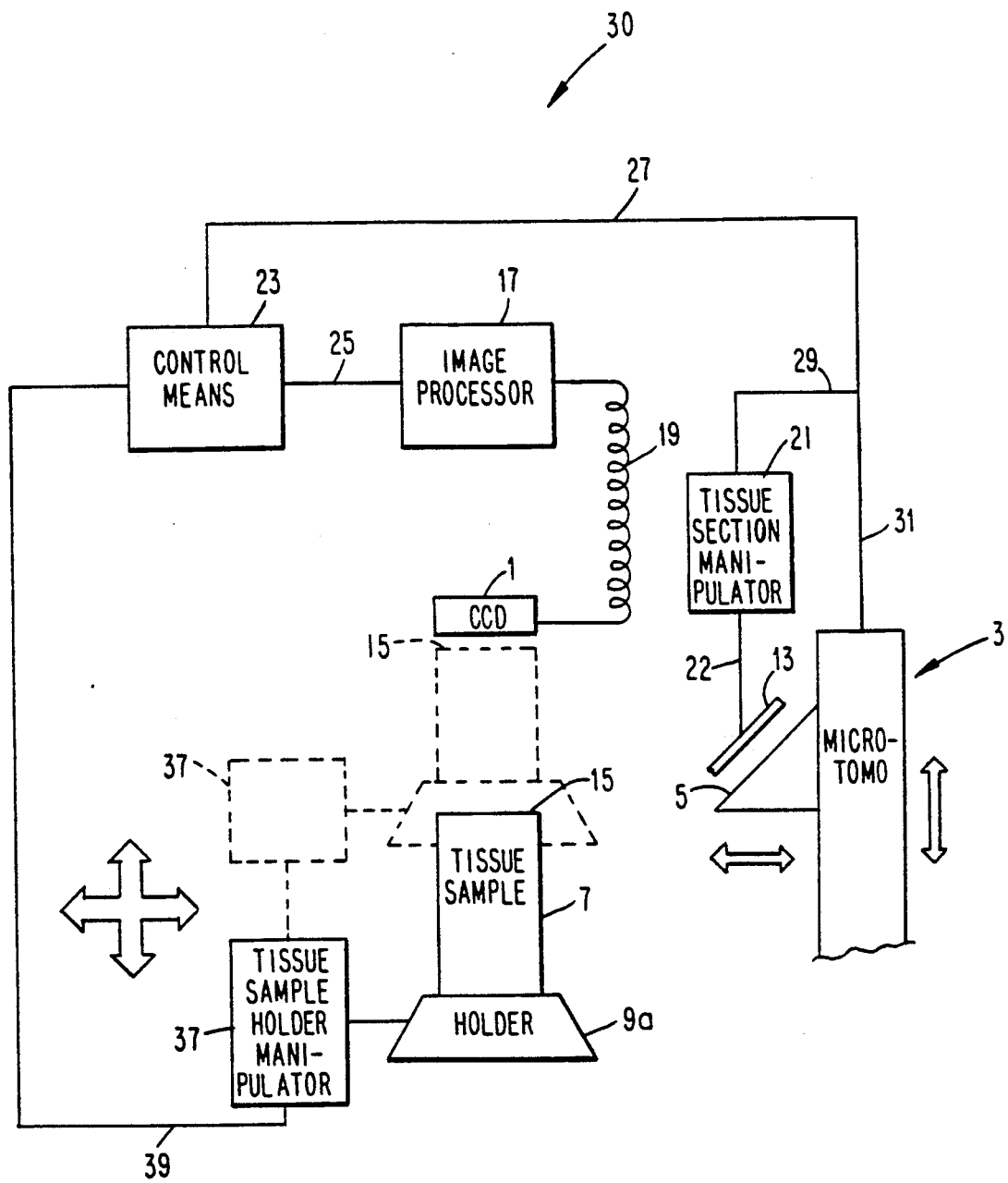
FIG. 3 shows a third embodiment of a three-dimensional autoradiographic imaging apparatus.

A third embodiment of the three-dimensional autoradiographical imaging system is depicted in FIG. 3 and is generally designated by the reference numeral 30. This system is similar to the first embodiment depicted in FIG. 1 with the addition of a tissue sample manipulating means 37. In this embodiment, the tissue sample manipulating means 37 is designed to raise and lower the tissue sample 7 towards the CCD 1. The tissue sample is raised to permit the CCD to read the top surface thereof and subsequently lowered to permit a further section to be removed by the microtome 3. This pattern of sequencing is continued until the entire tissue sample is read and sectioned. As shown in FIG. 3, the tissue manipulating means 37 can raise or lower the tissue sample and sample holder 9a in a vertical fashion and translate in a horizontal direction also. The tissue manipulating means is connected to the control means 23 by the connector 39.

Figure 4:
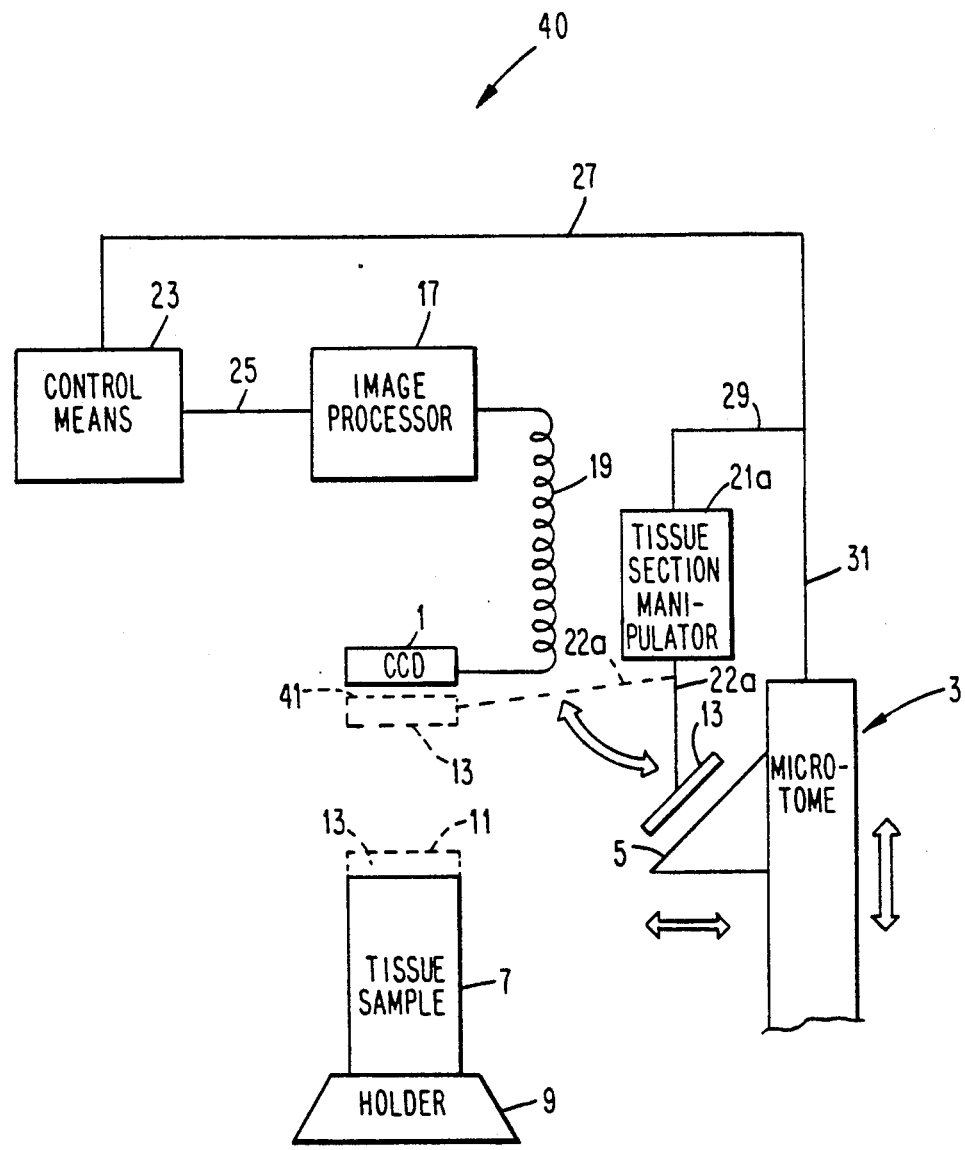
FIG. 4 shows a fourth embodiment of a three-dimensional autoradiographic imaging apparatus.

With reference to FIG. 4, a fourth embodiment of the three-dimensional autoradiographical imaging system is generally designated by the reference numeral 40 and is seen to include all of the basic components depicted in the embodiment depicted in FIG. 1. The fourth embodiment is designed to be used with tissue samples 7, which use higher levels of energy radiation which are capable of penetrating many microns or meters of tissue. In these radioactively tagged tissue samples, detection of the radioactively labeled substances in the tissue sample would not work in the embodiments depicted in FIGS. 1–3, since the elements in the CCD array would collect radiation from points throughout the entire tissue sample. This overall collection of radiation would lead to a blurred image. To overcome this problem, the three-dimensional autoradiographical imaging system is provided with a tissue section manipulating means 21a which is designed to juxtapose the section 13 to the CCD array 1. As can be seen from FIG. 4, the microtome 3 removes the section 13 from the tissue sample 1 and the manipulating arm 22a of the manipulating means 21a positions the tissue section 13 such that a surface 41 may be read by the charge coupled device 1. The tissue section 13 only contains radioactive sources in the plane of the section, thereby eliminating any effect of radioactive materials located within deeper sections of the tissue sample.

The tissue section manipulating means 21a may be any means that is capable of capturing the section 13 after it is removed by the microtome 3. For example, adhesive tape, sticky platens or slides, or by any other known mechanism that is capable of handling and manipulating a tissue section 13 in a position adjacent the charge coupled device 1. Another alternative includes floating the tissue section 13 in a water trough, as is commonly done in microtomes and, subsequently removing the section from the water trough and juxtaposing it to the CCD array.

It should also be understood that the manipulating means described above for the tissue sample and sample holder and the manipulating means for the charge coupled device may be of any known type capable of positioning these particular devices in predetermined positions. For example, actuators and mechanisms such as those employing motors, solenoids, hydraulics, pneumatics, hand cranks and/or combinations thereof may be utilized to achieve the desired movement and positioning with respect to the individual devices. In addition, although not shown, the various manipulating means may be combined in a single apparatus. For example, a three-dimensional autoradiographical imaging system may include both manipulating means for the tissue sample and sample holder, as well as the manipulating means for the charge coupled device and tissue section manipulating means capable of juxtaposing the tissue section in proximity to the CCD. An apparatus of this type would have the overall capability via the control means 23 to position one or a combination of the particular apparatus elements in a predetermined fashion to provide for an automated processing method to provide the desired three-dimensional image of the tissue sample.

In the embodiments depicted in FIGS. 1-4, additional means may be provided to clean the surface of the microtome and the charge coupled device. The cleaning means are adaptable to clean the surface of the CCD array after each exposure. For example, any known cleaning means, such as wipers or jets of fluid, may be used to clean the CCD surface. In addition, cleaning means may be provided to clean the surface of the knife 5 of the microtome 3 after each sectioning sequence. The microtome knife cleaning means may also be any type that is well known in the art.

Figure 5A:
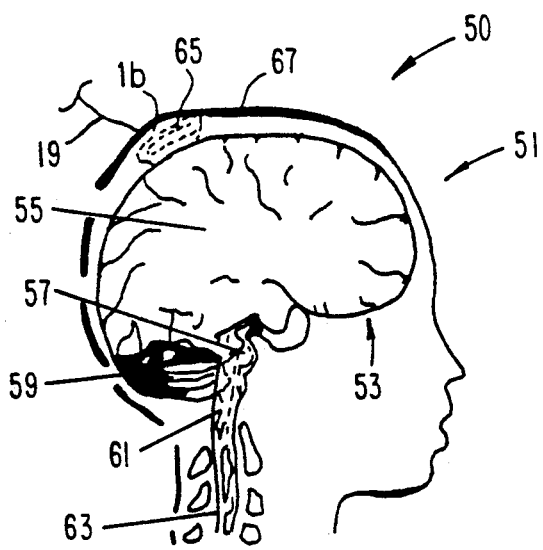
FIGS. 5(a)-(c) show a further aspect of a two-dimensional autoradiographic imaging system for brain activity depicting three embodiments utilizing a biocompatibly encapsulated charge coupled device.

In a further aspect of the invention, an in-vivo autoradiographic imaging is proposed for applications with the brains of humans or animals. In this system, two-dimensional imaging of metabolic or other biochemical/physiological parameters in the brains of humans and animals may be monitored over real-time. With reference to FIG. 5A, a first embodiment of the in-vivo autoradiographic imaging system is generally designated by the reference numeral 50 and is seen to include a human head 51 containing a brain 53. Also depicted are a cerebrum 55, a pons Varolii 57, a cerebellum 59, medulla oblongata 61 and spinal cord 63. In a first embodiment, a charge coupled device 1 contained within a biocompatible encapsulate 65 is placed within the skull portion 67 of the human head 51 and adjacent the brain 53. The CCD should be sufficiently near the brain to avoid blurring of an image produced by the CCD due to the thickness of the skull and related tissue. The charge coupled device 1 is electronically connected to an image processor such as that disclosed in the first embodiment depicted in FIG. 1 via the electrical connection 19. The image processor is capable of producing a two-dimensional image of the information received by the charge coupled device 1. In this embodiment, a radioactively labeled substance is administered either topically or systemically in the tissue to be imaged. The two-dimensional image produced by the CCD device is of high resolution, generally in the range of 1 to 100 microns, and may be continuously recorded by the image processor as changing patterns develop during brain activity. This real-time imagery is in contrast to conventional autographical systems which do not have the capability of imaging changing bio-chemical or physiological parameters over real-time. As described above, any known type radioactively tagged or labeled substances appropriate for use in monitoring brain activity in humans or animals may be utilized as a radiation-emitting source for detection by the CCD. The biocompatibly encapsulated material 65 may be any known type typically used in clinical or medical applications. For example, a silicone type material or other inert substance may be used.

Figure 5B:
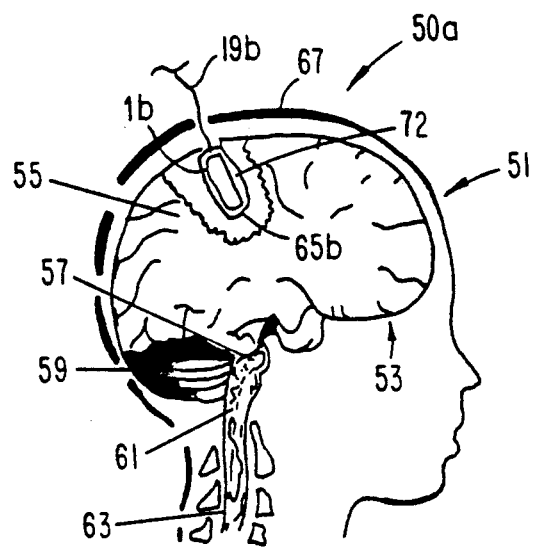

With reference to FIG. 5B, a second embodiment of the in-vivo autoradiographical imaging system is depicted and is generally designated by the reference numeral 50A. In this embodiment, a CCD device $1b$ may be surgically implanted within the brain tissue itself by incision such that internal surfaces may be accessed. In this configuration, the electrical connection $19b$ extends out from the CCD through the brain tissue and skull 67 to the image processor 17 (not shown). Again, the CCD $1b$ is contained within a biocompatible encapsulant $65b$ as shown in the embodiment depicted in FIG. 5A. The bioencapsulant should be very thin, for example, on the order of the pixel spacing or less, on the active surface of the CCD to avoid unnecessary attenuation of the beta rays.

Figure 5C:
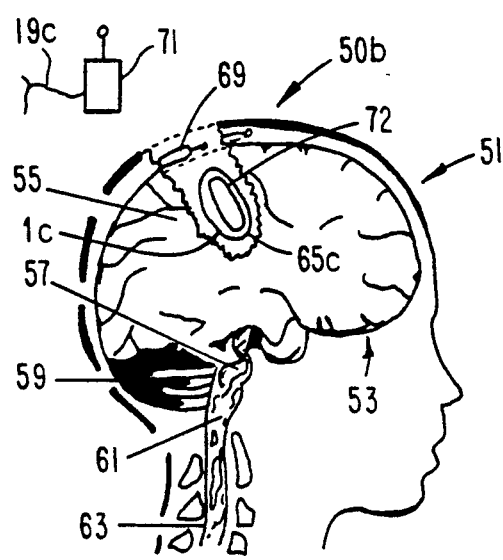

A third embodiment of the in-vivo autoradiographical imaging system is depicted in FIG. 5C and is generally designated by the reference numeral $50b$. In this embodiment, a CCD $1c$, surrounded by a biocompatible encapsulant $65c$, is again implanted within the brain 53. The charge coupled device $1c$ is electrically connected to a transmitter 69 via the connector 68. The transmitter 69 receives the information detected by the charge coupled device $1c$ and transmits the information to the receiver 71. The receiver 71 then transmits the information received from the transmitter by the connector $19c$ to the image processor 17 (not shown). In this manner, the electrical connection $19b$ depicted in the embodiment shown in FIG. $5b$ is eliminated through the use of the combination of the transmitter 69 and the receiver 71. Thus, the charge coupled device may be implanted into portions of the brain tissue which may not permit an electrical connector such as $19b$ from extending through the brain tissue and out the skull portion to an image processor.

With reference to FIGS. 5B and 5C, the implanted CCD includes a shield 72 which prevents background signal in the CCD derived from radiation coming from the backside of the CCD.

By providing the charge coupled device in juxtaposition with a portion of brain tissue which contains a radioactively labeled or tagged substance, continuous monitoring of metabolic or physiological parameters may be performed for clinical or behavioral studies. A two-dimensional image is produced which provides real-time imagery of these changing functions which permit the monitoring of brain activity.

Regarding the real-time imaging of brain activity, a specific embodiment will be now described. A radioactive substance such as, but not limited to, fluorodeoxyglucose for studying local cerebral metabolic activity, may be injected systemically or applied topically to a tissue site. Alternatively, a substance that will preferentially label tumors such as a cancer-resistor marked with a radio-isotope or a deoxyglucose can be injected systemically or applied topically. The brain activity will be revealed by means of using the detected radioactivity in consort with kinetic equations such as the Sokoloff Equation, which are well accepted in the biomedical literature.

Of course, it should be understood that the real-time imaging embodiment of the present invention is not limited to brain tissue, but may also include tissue such as muscle, kidney, other organs, etc.

In the in-vivo autoradiographical imaging system, low-energy beta rays that may only come from tissue adjacent the CCD is preferred to avoid blurring as a result of higher energy radioactive material affecting the imaging process from tissue removed from the CCD.

In a third aspect of the present invention, a two-dimensional imaging charge coupled device is used as one wall of a micro two-dimensional gel electrophoresis chamber. Imaging screens for detecting and storing information corresponding to a pattern of emission from an electrophoresis gel containing radioactively labeled substances are known, as exemplified by U.S. Pat. No. 5,028,793 to Lindmayer et al. as discussed hereinabove. In these applications, a protein or other analyte is labeled with an appropriate radioisotope, such as a low-energy beta particle, for attracting movement of the radioactively labeled substances within the electrophoresis gel. Using a two-dimensional charge coupled device in combination with an electrophoresis gel containing a radioactively labeled substance permits use of very small sample volumes. In addition, automatic end point detection is possible, which optimizes the number of runs necessary to obtain the desired data. Furthermore, no post-run development, such as staining, is required when using the inventive combination.

Figure 6:
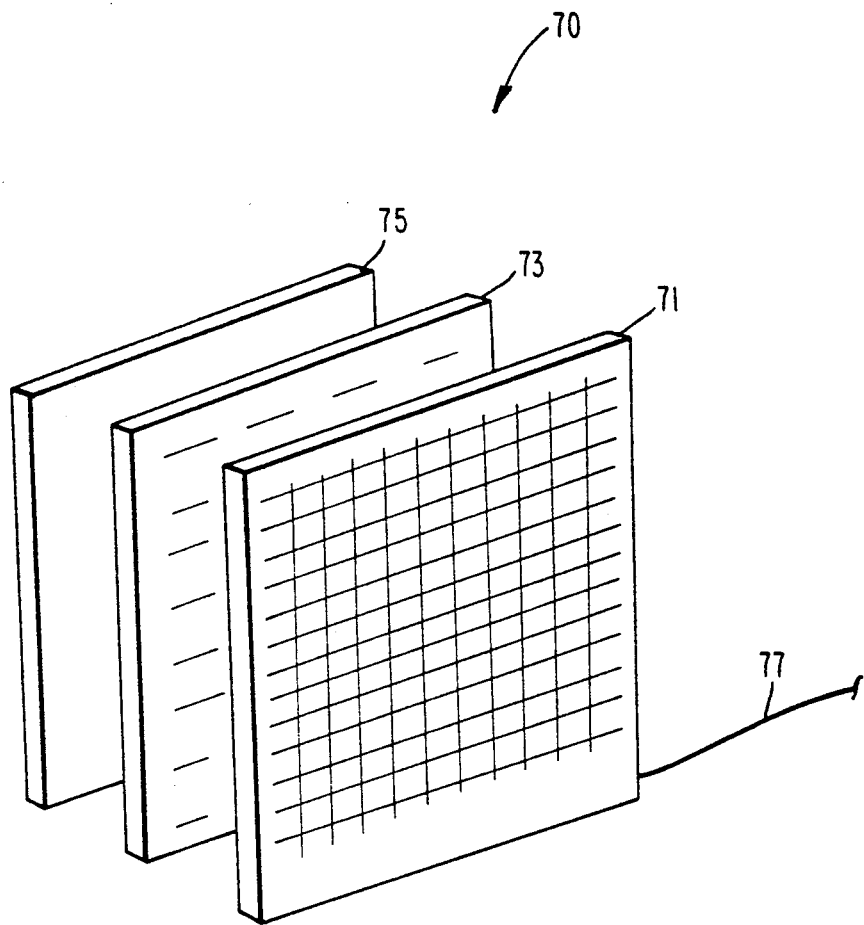
FIG. 6 shows a schematic representation of a gel electrophoresis chamber utilizing a charge coupled device to detect a radioactively labeled substance within the electrophoresis gel.

With reference to FIG. 6, an exploded view of a typical microelectrophoresis gel chamber is shown and is generally designated by the reference numeral 70. The chamber is seen to include a charge coupled device 71 adjacent an electrophoresis gel containing a radioactively labeled substance therein and a passive wall 75. It should be noted that the CCD can actually form one or both of the walls of the electrophoresis chamber to bring the CCD(s) in intimate contact with the gel. The charge coupled device is electrically connected to an image processor via the connector 77. The image processor is similar to that disclosed for the in-vivo autoradiographical imaging system as described hereinabove which produces a two-dimensional image of the information detected by the charge coupled device. In an exemplary use, the gel could be a standard SDS gel or agarose gel (both well known in the art). The gel could be of the well known two-dimensional or one dimensional type, and could be microminiaturized to the size of a typical CCD chip, providing further advantages of speed and low power consumption. An example of a specific tag for proteins would include $^{35}$S or $^{32}$P.

Although a gel electrophoresis chamber is depicted in combination with the charge coupled device 71, alternating field electrophoresis or other types of electrophoresis and chromatography as are well known in the prior art may be utilized in conjunction with the disclosed charge coupled device. For example, a one-dimensional array CCD could be used to scan a one-dimensional electrophoresis apparatus.

In a further aspect of the present invention, two or more different energies of radiation may be used for detection by the CCD. Use of two or more different energies of radiation are applicable to the embodiment of the invention which produces a three-dimensional image of a radioactively tagged substance, the real-time imaging aspect or as applied to the migrating analytes in the case of electrophoresis. In each case, for example, two different substances may be injected in the particular tissue, tissue sample, or electrophoresis gel. Each substance would have a different preferential location or biochemical activity and would also have a different characteristic radiation energy. In order to detect both the high and low energy radiation energy, selected pixels of the CCD may be covered with a filter to block the low energy rays. Blocking the low energy rays would result in obtaining the high energy count. Subtraction of the high energy only count at each covered pixel from the total count at the adjacent uncovered pixel location would provide the low energy count at that location. In this manner, two different locations may be monitored in a tissue sample, a plurality of metabolic or biochemical parameters during real-time imagery may be monitored during real-time imagery, or different radioactively tagged analytes may be imaged during electrophoresis processes.

In an alternative embodiment, instead of blocking the individual pixels which would normally be done during the charge coupled device manufacturing process, as is well known in the art, the charge coupled device could be covered with the appropriate filter to block the low energy rays. By using a filter, the same detection of the high energy count followed by subtraction to achieve the low energy count would provide monitoring of the different levels of radiation energy. It should be understood that blocking individual pixels or providing filters for CCDs to block out specific levels of energy are well recognized in the prior art. Although the use of two different levels of radiation energy have been disclosed, it should be understood that more than two different energies of radiation may also be utilized in conjunction with the autoradiographical imaging of the present invention.

Although a charge coupled device has been disclosed as a solid state radiation detecting means for detecting the radioactively tagged substance or tissue in the present invention, a charge injection device or a self-scan photodiode array may also be utilized to achieve the desired detection of radiation. The charge injection device or self-scan photodiode array may be utilized in the three-dimensional autoradiographic imaging system, the real-time imaging of metabolic or biochemical parameters in tissue of humans or animals, or in conjunction with radioactively tagged analytes in electrophoresis or chromatographic applications.

As such, an invention has been disclosed in terms of preferred embodiments thereof which fulfills each and every one of the objects of the present invention as set forth hereinabove and provides a new and improved two- and three-dimensional autoradiographical imaging system utilizing charge coupled devices.

Of course, various changes, modifications and alterations in the teachings of the present invention may be contemplated by those skilled in the art without departing from the intended spirit and scope thereof. As such, it is intended that the present invention only be limited by the terms of the appended claims.

We claim:

1. An apparatus for producing a three-dimensional autoradiographical image of a tissue sample containing a radioactively tagged substance comprising:
   a) a solid state radiation detecting means for detecting said radioactively tagged substance in said tissue sample;
   b) means for sectioning said tissue sample to provide a section of tissue sample having a first surface and thereby providing a further exposed surface on said tissue sample;
   c) means for processing information generated by said solid state radiation detecting means into a plurality of two-dimensional images and for further processing said plurality of two-dimensional images into said three-dimensional image of said tissue sample;

d) manipulating means for positioning said section of said tissue sample in a predetermined location;

e) control means for controlling said solid state radiation detecting means, said means for processing information generated by said solid state radiation detecting means, said means for sectioning and said manipulating means to automatically analyze said tissue sample and produce said three-dimensional image of said tissue sample containing said radioactively tagged substance.

2. The apparatus of claim 1, wherein said means for sectioning further comprises a microtome.

3. The apparatus of claim 1 further comprising means to manipulate said solid state radiation detecting means to juxtapose said solid state radiation detecting means adjacent said first surface or said further exposed surface to permit said solid state radiation detecting means to detect said radioactively tagged substance therein.

4. The apparatus of claim 3 further comprising means to manipulate said tissue sample to juxtapose said first surface or said further exposed surface adjacent said solid state radiation detecting means to permit said solid state radiation detecting means to detect said radioactively tagged substance therein.

5. The apparatus of claim 1 further comprising means to manipulate said tissue sample to juxtapose said first surface or said further exposed surface adjacent said solid state radiation detecting means to permit said solid state radiation detecting means to detect said radioactively tagged substance therein.

6. The apparatus of claim 5 wherein said means to manipulate further includes a tissue sample holder.

7. The apparatus of claim 1 wherein said manipulating means includes means to manipulate said section such that said section is juxtaposed adjacent said solid state radiation detecting means to permit said solid state radiation detecting means to detect said radioactively tagged substance in said section.

8. The apparatus of claim 7 further comprising means to manipulate said solid state radiation detecting means to juxtapose said solid state radiation detecting means adjacent said first surface or said further exposed surface to permit said solid state radiation detecting means to detect said radioactively tagged substance therein.

9. The apparatus of claim 7 further comprising means to manipulate said tissue sample to juxtapose said further exposed surface adjacent said solid state radiation detecting means to permit said solid state radiation detecting means to detect said radioactively tagged substance therein.

10. The apparatus of claim 1 further comprising cleaning means to clean said solid state radiation detecting means after said radioactively tagged substance has been detected.

11. The apparatus of claim 1 further comprising cleaning means for cleaning said means for sectioning after said tissue sample has been sectioned.

12. The apparatus of claim 1 wherein said solid state radiation detecting means is selected from the group consisting of a charge coupled device, a charge injection device and a self-scanning photodiode array.

13. The apparatus of claim 1, wherein said solid state detecting means includes means for detecting at least two different levels of radiation in said radioactively tagged substance.

14. The method of producing a three-dimensional autoradiographical image of a tissue sample containing a radioactively tagged substance comprising the steps of:

a) providing a tissue sample containing a radioactively tagged substance;

b) providing a solid state radiation detecting means;

c) detecting said radioactively tagged substance on a top surface of said tissue sample using said solid state radiation detecting means and producing a first two-dimensional image thereof;

d) removing a section of said tissue sample and exposing a further surface of said tissue sample;

e) detecting said radioactively tagged substance in said further surface using said solid state radiation detecting means and producing a second two-dimensional image thereof;

f) repeating steps (d) and (e) to produce further surfaces of said tissue sample so as to produce a plurality of two-dimensional images of each of said further surfaces; and g) processing each of said two-dimensional images to produce a three-dimensional image of said tissue sample containing said radioactively tagged substance.

15. The method of claim 14 further comprising the step of manipulating said solid state radiation detecting means to juxtapose said solid state radiation detecting means adjacent said top surface or one of said further surfaces of said tissue sample to facilitate detection of said radioactively tagged substance.

16. The method of claim 15 further comprising the step of manipulating said tissue sample to further juxtapose said top surface or one of said further surfaces of said tissue sample to facilitate detection of said radioactively tagged substance.

17. The method of claim 14 further comprising the step of manipulating said tissue sample to juxtapose said top surface or one of said further surfaces of said tissue sample to facilitate detection of said radioactively tagged substance.

18. The method of claim 14 further comprising the step of providing a microtome for removing said section of said tissue sample.

19. The method of claim 14, further comprising the step of providing said solid state radiation detecting means selected from the group consisting of a charge coupled device, a charge injection device and a self-scanning photodiode array.

20. The method of claim 14, further comprising the step of providing said solid state radiation detecting means with means for detecting at least two different levels of radiation in said radioactively tagged substance.

21. The method of producing a three-dimensional autoradiographical image of a tissue sample containing a radioactively tagged substance comprising the steps of:

a) providing a tissue sample containing a radioactively tagged substance;

b) providing a solid state radiation detecting means;

c) removing a section of said tissue sample and exposing a further surface of said tissue sample;

d) detecting said radioactively tagged substance in said section of said tissue sample using said solid state radiation detecting means and producing a two-dimensional image thereof;

e) repeating steps of (c) and (d) to produce a plurality of said sections of said tissue sample and a plurality of two-dimensional images from said plurality of said sections; and f) processing said plurality of two-dimensional images to produce the three-dimensional image of said tissue sample containing said radioactively tagged substance.

22. The method of claim 21 further comprising the step of manipulating said solid state radiation detecting means to juxtapose said solid state radiation detecting means adjacent one of said sections of said tissue sample to facilitate detection of said radioactively tagged substance in said section.

23. The method of claim 21 further comprising the step of manipulating one of said sections to juxtapose one of said sections adjacent said solid state radiation detecting means to facilitate detection of said radioactively tagged substance in said section.

24. The method of claim 21 further comprising the step of providing a microtome for removing said sections from said tissue sample.

25. The method of claim 21, further comprising the step of providing said solid state radiation detecting means selected from the group consisting of a charge coupled device, a charge injection device and a self-scanning photodiode array.

26. The method of claim 21, further comprising the step of providing said solid state radiation detecting with means for detecting at least two different levels of radiation in said radioactively tagged substance.

* * * * *